US005231983A

United States Patent [19]

[11] Patent Number: 5,231,983
[45] Date of Patent: Aug. 3, 1993

Matson et al.

[54] METHOD OF AND APPARATUS FOR THE AEROSOL ADMINISTRATION OF MEDICATION

[75] Inventors: Charles J. Matson, Stillwater; David J. Velasquez, Randolph, both of Minn.

[73] Assignee: Minnesota Mining and Manufacturing, St. Paul, Minn.

[21] Appl. No.: 771,825

[22] Filed: Oct. 7, 1991

Related U.S. Application Data

[63] Continuation of Ser. No. 460,315, Jan. 3, 1990, abandoned.

[51] Int. Cl.[5] .......... A61M 16/00

[52] U.S. Cl. .......... 128/207.14; 128/207.15; 128/200.23

[58] Field of Search .......... 128/200.14, 203.12, 128/204.25, 207.14, 207.15, 200.23

[56] References Cited

U.S. PATENT DOCUMENTS

| | | | |
|---|---|---|---|
| 440,713 | 11/1890 | Krohne et al. | 128/206.28 |
| 2,843,119 | 7/1958 | Glasser | 128/142 |
| 3,456,646 | 7/1969 | Phillips et al. | 128/173 |
| 3,738,542 | 6/1973 | Ruscitti | 222/402.16 |
| 3,881,479 | 5/1975 | Carden | 128/145.8 |
| 3,915,165 | 10/1975 | Rambosek et al. | 128/145.8 |
| 4,119,101 | 10/1978 | Igich | 128/351 |
| 4,143,658 | 3/1979 | Rambosek et al. | 128/184 |
| 4,186,737 | 2/1980 | Valenta et al. | 128/203.28 |
| 4,192,860 | 3/1980 | Griffiths | 424/43 |
| 4,270,530 | 6/1981 | Baum et al. | 128/204.25 |
| 4,327,721 | 5/1982 | Goldin et al. | 128/207.15 |
| 4,343,304 | 8/1982 | Hickmann | 128/200.14 |
| 4,396,015 | 8/1983 | Johnson | 128/200.14 |
| 4,407,481 | 10/1983 | Bolton et al. | 251/353 |
| 4,413,755 | 11/1983 | Brunet | 222/402.12 |
| 4,452,241 | 6/1984 | Sarnoff et al. | 128/204.18 |
| 4,484,577 | 11/1984 | Sackner et al. | 128/203.28 |
| 4,519,388 | 5/1985 | Schwanbom et al. | 128/204.25 |
| 4,534,343 | 8/1985 | Nowacki et al. | 128/200.23 |
| 4,546,768 | 10/1985 | Ferierabend | 128/200.16 |
| 4,584,997 | 4/1986 | Delong | 128/205.23 |
| 4,637,389 | 1/1987 | Heyden | 128/207.15 |
| 4,646,733 | 3/1987 | Stroh et al. | 128/207.16 |
| 4,664,107 | 5/1987 | Wass | 128/200.23 |
| 4,669,463 | 6/1987 | McConnell | 128/207.14 |
| 4,693,243 | 9/1987 | Buras | 128/207.15 |
| 4,722,334 | 2/1988 | Blackmer et al. | 128/203.16 |
| 4,790,305 | 12/1988 | Zoltan et al. | 128/200.23 |
| 4,819,664 | 4/1989 | Nazari | 128/207.15 |
| 4,819,834 | 4/1989 | Theil | 222/355 |

(List continued on next page.)

FOREIGN PATENT DOCUMENTS

| | | |
|---|---|---|
| 0245607-A2 | 11/1987 | European Pat. Off. . |
| 3608943 | 2/1987 | Fed. Rep. of Germany . |
| WO89/05670 | 6/1989 | PCT Int'l Appl. . |

OTHER PUBLICATIONS

*Intratracheal jet Kanamycin Toyo*, Package insert.
Model #9056 Bronchodilator Tee; Boehringer Laboratories Inc. Wynnewood, Pa. Cart Frame 9055-482.

(List continued on next page.)

*Primary Examiner*—Edgar S. Burr
*Assistant Examiner*—Aaron J. Lewis
*Attorney, Agent, or Firm*—Gary L. Griswold; Walter N. Kirn; Jeffrey J. Hohenshell

[57] ABSTRACT

A method and apparatus for the aerosol administration of medication. The method comprises the steps of inserting an endotracheal tube into the trachea of a patient, establishing an air flow through the endotracheal tube, and injecting medication into the air flow inside the endotracheal tube in an aerosol form. The apparatus comprises an improved endotracheal tube adapted for the aerosol administration of medication, the endotracheal tube having an aerosol medication lumen, having proximal and distal ends, and extending along at least a portion of the endotracheal tube. A nozzle is located at the distal end of the lumen, inside the endotracheal tube, but adjacent its distal end. A connector is located at the proximal end of the lumen to a connect the lumen to a supply of aerosol medication, to dispense the medication in aerosol form from the nozzle in the endotracheal tube.

12 Claims, 2 Drawing Sheets

U.S. PATENT DOCUMENTS

| | | | |
|---|---|---|---|
| 4,821,714 | 4/1989 | Smelser | 128/207.14 |
| 4,840,172 | 6/1989 | Augustine et al. | 128/207.14 |
| 4,840,173 | 6/1989 | Porter, III | 128/207.15 |
| 4,881,542 | 11/1989 | Schmidt et al. | 128/207.14 |
| 4,938,210 | 7/1990 | Shane | 128/203.12 |
| 4,953,546 | 9/1990 | Blackmer et al. | 128/203.16 |
| 4,955,375 | 9/1990 | Martinez | 128/207.15 |
| 4,960,122 | 10/1990 | Mizus | 128/207 |
| 4,969,878 | 11/1990 | Schmidt et al. | 604/264 |
| 4,977,894 | 12/1990 | Davies | 128/207 |
| 5,078,131 | 1/1992 | Foley | 128/203.15 |

OTHER PUBLICATIONS

Summary of Toyojozo to Market Device for Treatment of Pneumonia.

Airway reactivity in ponies with recurrent airway obstruction (heaves), F. J. Dirksen et al., Journal of Applied Physiology 58(2): 598–604 (1985).

Aerosol delivery in intubated, mechanically ventilated patients; MacIntyre et al. Critical Care Medicine, 13:81–84 (Feb. 1985).

M. J. Diamon, Letter to Editor; "Delivering Bronchodilators into the Anesthesia Circuit": Anesthesiology 64:531 (Apr. 1986).

Redding et al., Effective Routes of Drug Administration During Cardiac Arrest, Mar.–Apr. 1967.

Feferman et al., A Simple Method for Administering Endotracheal Medication, Mar. 1983.

Greenberg, Endotracheal Drugs: State of the Art, Sep. 1984.

Greenberg et al., Comparison of Deep and Shallow Endotracheal Administration of Dionosil in Dogs and Effect of Manual Hyperventilation, Mar. 1985.

Hasegawa, The Endotrachael Use of Emergency Drugs, Jan. 1986.

Ahrens et al., The Delivery of Therapeutic Aerosols Through Endotracheal Tubes, Jan.–Feb. 1986.

Diamond, Delivering Bronchodilators into the Anesthesia Circuit, Apr. 1986.

Steedman et al., Emergency Endotracheal Drug Administration Using Aerosol, 1987.

Frass et al., Evaluation of Esophageal Tracheal Combitube in Cardiopulmonary Resuscitation, Jun. 1987.

Frass et al., The Esophageal Trachael Combitube: Preliminary Results With a New Airway for CPR, 1987.

Greenberg, The Use of Endotracheal Medication in Cardiac Emergencies, 1984.

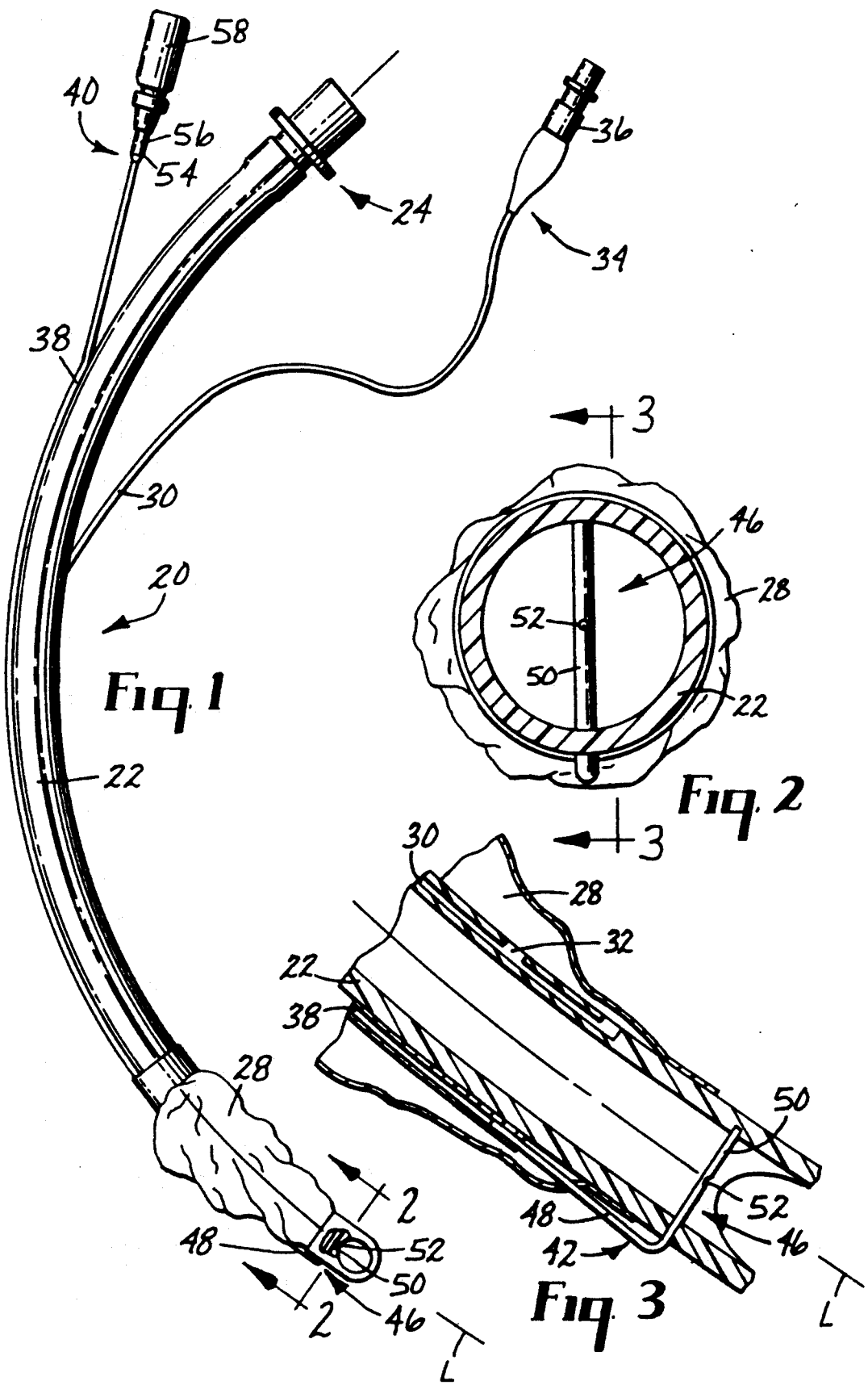

METHOD OF AND APPARATUS FOR THE AEROSOL ADMINISTRATION OF MEDICATION

This is a continuation of application Ser. No. 07/460,315 filed Jan. 3, 1990, now abandoned.

BACKGROUND OF THE INVENTION

This invention relates to a method of and apparatus for the administration of medication, and in particular to the aerosol administration of medication through an endotracheal tube.

The primary goal of emergency therapy is to quickly and efficiently deliver the medication required during the crisis period. In many emergency situations the selection of the route of administration can be nearly as important as the selection of the medication. For example, while prompt intravenous administration of medication is usually the first choice, it is often not possible because of cardiovascular collapse which prevents the placement of either peripheral or central venous catheters.

The establishment of a patient airway, for example with an endotracheal tube, is usually the first action taken during emergency treatment. The endotracheal tube provides a route for the administration of injectable medication. By injecting medication in liquid form from a syringe into the central bore of an endotracheal tube, the medication is deposited on the epithelial surface of the upper airways and absorbed into the bronchial and pulmonary circulation. This method of administration of medication in liquid form has some disadvantages: some of the liquid medication is lost on the interior surface of the endotracheal tube; the liquid medication is distributed over only a relatively small portion of the available pulmonary surfaces, delaying uptake and limiting the dosage that can be administered; it is time consuming to dilute the medication and load the syringe; and the use of this method of administration may require the interruption of CPR efforts.

Various endotracheal tubes have been constructed to facilitate the delivery of liquid medication through the endotracheal tube. For example the devices disclosed in U.S. Pat. Nos. 4,119,101, 4,669,463, and 4,821,714 each provide for the administration of medication in liquid form via an endotracheal tube. However, these devices still suffer from the same disadvantages associated with the administration of medication in liquid form discussed above.

SUMMARY OF THE INVENTION

The present invention involves administering medication in aerosol form through an endotracheal tube, and therefore alleviates some of the disadvantages encountered with the administration of liquid medication through an endotracheal tube. The aerosol administration of medication reduces the amount of medication lost on the interior surfaces of the endotracheal tube, and it permits the medication to be distributed over a larger surface area, speeding uptake and permitting larger dosages to be administered. The aerosol medication can be provided in pre-loaded canisters, since dilution is not critical, thereby saving the time required for diluting and loading syringes with liquid medication. Finally, the aerosol administration of medication need not interfere with on-going CPR efforts.

According to the method of this invention, medication is administered by inserting an endotracheal tube into the patient's trachea, and injecting medication in aerosol form into the air stream in the endotracheal tube. The medication is preferably injected at the center of the endotracheal tube in order to maximize its entrainment in the air stream and to minimize the deposition of the medication on the sidewalls of the tube.

The apparatus of this invention is adapted for injecting medication in aerosol form into the air stream in an endotracheal tube. Generally, the apparatus comprises an improved endotracheal tube of the type comprising a hollow tube body having a proximal end, and a distal end adapted for insertion into the patient's trachea. The apparatus further comprises an aerosol medication lumen, having a proximal end and a distal end, and running at least partly along the endotracheal tube. An aerosol nozzle is disposed at the distal end of the medication lumen, inside the tube but adjacent its distal end. A connector is provided on the proximal end of the medication lumen for connecting to an aerosol canister of medication to provide the medication to the medication lumen for ejection in aerosol form from the nozzle.

Thus, the method and apparatus of this invention provide for the injection of medication in aerosol form into the air stream in an endotracheal tube, providing for better distribution of the medication over the pulmonary surfaces than can be achieved with the administration of liquid medication. This better distribution speeds uptake of the medication, and allows larger doses to be administered. Because the medication is in aerosol, rather than liquid form, less medication is lost on the surfaces of the endotracheal tube. The aerosol administration permits the use of metered dose canisters that eliminate mixing and measuring delays experienced with liquid medications. Finally, aerosol administration does not interfere with on-going CPR efforts.

These and other advantages will be in part apparent, and in part pointed out hereinafter.

BRIEF DESCRIPTION OF THE DRAWINGS

FIG. 1 is a side elevation view of an improved endotracheal tube constructed according to the principles of this invention, and adapted for use in the method of this invention;

FIG. 2 is an enlarged transverse cross-sectional view of the improved endotracheal tube taken along the plane of line 2—2 in FIG. 1;

FIG. 3 is a longitudinal cross-sectional view of the improved endotracheal tube taken along the plane of line 3—3 in FIG. 2.

Corresponding reference numerals indicate corresponding parts throughout the several view of the drawings.

DETAILED DESCRIPTION OF THE PREFERRED EMBODIMENT

Figure 4:
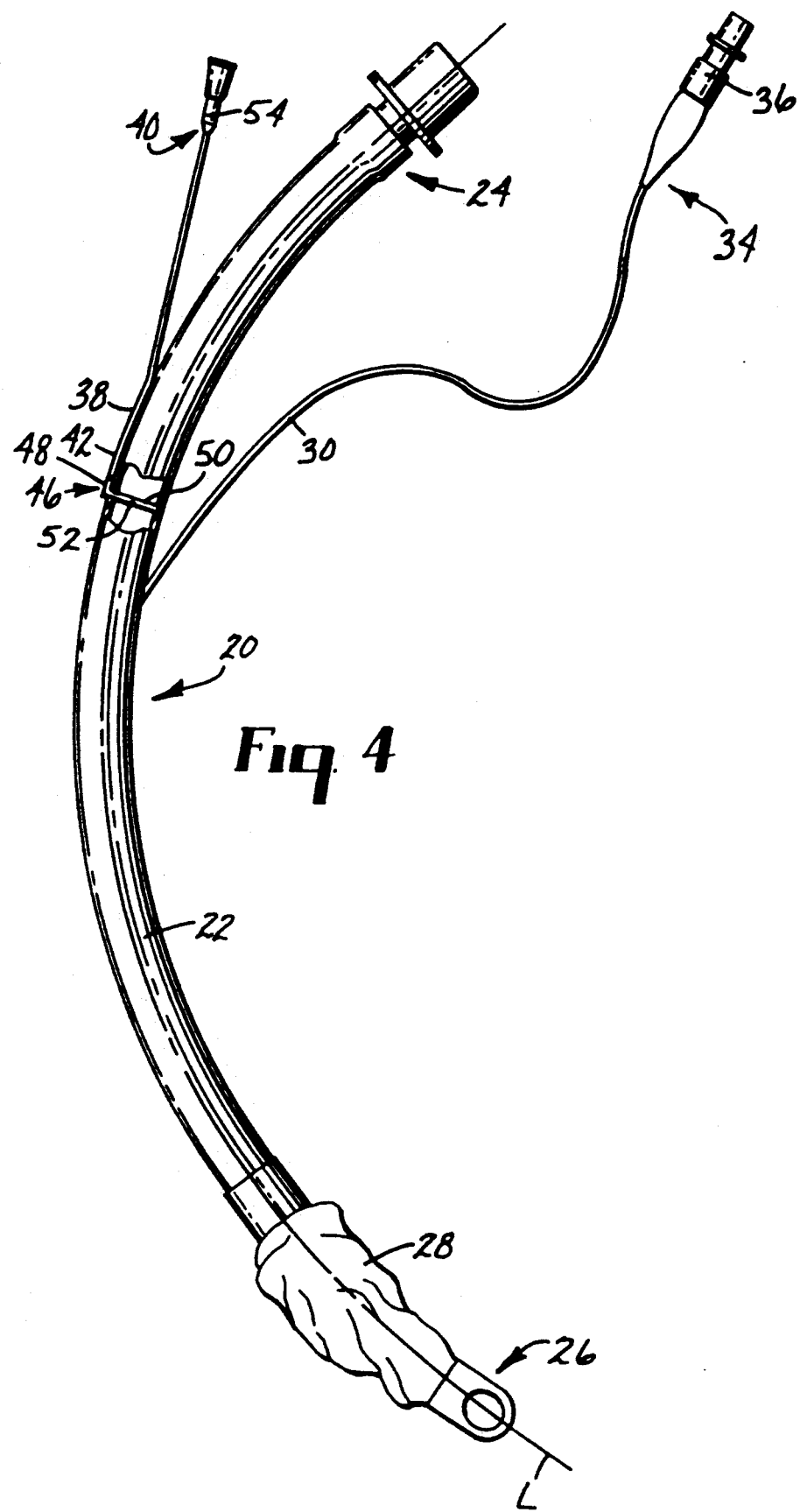
FIG. 4 is a side elevation view of a second embodiment of the improved endotracheal tube constructed according to the principles of this invention.

A first embodiment of an improved endotracheal tube constructed according to the principles of this invention is indicated generally as 20 in FIG. 1. The endotracheal tube 20 is generally of standard construction, comprising a hollow tubular body 22, preferably made of a flexible plastic material. The body 22 has a proximal end 24, and a distal end 26 that is adapted for insertion into the trachea of a patient, and having a longitudinal axis L extending between proximal and distal ends 24 and 26. For this purpose, the distal end 26 has a rounded tapering configuration. As is well known in the art, the endotracheal tube 20 may include an inflatable balloon 28 on its exterior, adjacent its distal end, and a lumen 30 extending substantially along the length of the endotracheal tube. The distal end 32 of the lumen 30 communicates with the balloon 28, and the proximal end 34 of the lumen 30 has a connector 36, adapted for connection to an air supply to inflate the balloon 28.

However, unlike a conventional endotracheal tube, the endotracheal tube 20 has an aerosol medication lumen 38, having a proximal end 40 and a distal end 42. The medication lumen 38 is preferably made from a flexible chemically-inert (i.e., inert to the medications to be delivered) polymeric material so that it can flex with the endotracheal tube, although it could be made of some other suitable material. The medication lumen 38 extends along at least a portion of the tubular body 22, and may be located inside the body, outside the body, or inside the wall of the body. The distal end 42 of the medication lumen 38 preferably terminates in an injector 46. The injector 46 comprises a first portion 48 extending generally parallel with the tubular body 22, and a second portion 50 extending generally chordally (and more preferably diametrically) across the interior of the tubular body 22, closely adjacent the distal end of the tubular body. The injector 46 is preferably a small diameter, L-shaped hollow metal tube. A nozzle 52 is preferably located in the middle of the second portion 50 of the injector 46, at the center (as considered in transverse cross-section) of the tubular body. The nozzle 52 is preferably oriented to face outwardly from the distal end of the endotracheal tube 20.

There is preferably some means, such as connector 54 for connecting the proximal end 40 of the medication lumen 38 to the valve and stem 56 of a canister 58 of aerosol medication, so that actuation of the canister 58 releases the medication into the medication lumen 38. The canister 58 is preferably of the type that can dispense metered doses upon actuation. These canisters typically contain multiple doses of a medication and are equipped with a metering valve to regulate the dosage. These valves are designed to deliver a predetermined volume of the aerosol formulation, e.g., 50 or 63 microliters, each time the valve is actuated. The lumen 38 conducts the medication under pressure to the nozzle 52, from which it is ejected as an aerosol into the air stream passing through the endotracheal tube 20. The generally central location of the nozzle 52 and its location adjacent the distal end of the endotracheal tube 22 causes most of the medication to be entrained in the air stream, with relatively little of the medication being deposited on the walls of the endotracheal tube.

The length and internal size of the lumen 38, the length and internal size of the injector 46, and the size of the nozzle 52 are all adjusted to achieve the best aerosol dispersion of the medication. Experiments indicate that greater efficiencies in delivery are achieved with larger dose sizes. Experiments have also indicated that better aerosol delivery is seen at smaller nozzle diameter (e.g., 5 mil) or larger nozzle diameter (e.g., 81 or 100 mil) but not at intermediate sizes. The appropriate orifice diameter, lumen diameter and lumen length for a given dosage are easily determined by testing. The following table tabulates the results of testing conducted by the inventors:

| Remote Nozzle Geometries and Aerosol Outputs | | | |
| --- | --- | --- | --- |
| Orifice diameter (mils) | Lumen diameter (mm) | Lumen length (mm) | Aerosol output:** Respirable mass (mg/m$^3$) |
| 100 | 2.92 | 152.4 | 2.6,3.5,3.4,2.8 |
| 81 | 2.92 | 152.4 | 0.3,0.4,0.3,0.9 |
| 50 | 1.57 | 152.4 | 0.1,0.1,0.1,2.5 |
| 33 | 1.19 | 152.4 | 0.1,0.3,1.3,59.2 |
| 23 | 1.14 | 152.4 | 0.1,0.1,0.3,7.8 |
| 13 | 1.14 | 152.4 | 0.0,0.0,0.0,34.1 |
| 5 | 1.14 | 152.4 | 0.1,0.1,0.1,27.0 |
| 100 | 2.92 | 304.8 | 3.3,4.4,3.2,4.0 |
| 81 | 2.92 | 304.8 | 1.1,1.0,0.7,1.0 |
| 50 | 1.57 | 304.8 | 0.1,0.1,0.0,0.0 |
| 33 | 1.19 | 304.8 | 0.0,0.0,0.0,0.1 |
| 23 | 1.14 | 304.8 | 0.0,0.0,0.2,3.3 |
| 13 | 1.14 | 304.8 | 0.0,0.0,0.0,0.0 |
| 5 | 1.14 | 304.8 | 0.2,0.1,0.0,31.0 |

**Aerosol output is reported as four values indicating output from four different MDI valve volumes: 25 ul, 50 ul, 63 ul, and 100 ul.

According to the method of aerosol administration of medication of the present invention, the endotracheal tube body 22 is first inserted into the trachea of the patient to establish an air supply to the patient's lungs. Then, when medication is needed, connector 54 is connected to the valve and stem 56 of a canister 58 of the medication. The valve and stem 56 are actuated, and medication is delivered to the medication lumen 38, where it passes under pressure to the injector 46. The medication is ejected in aerosol form from the nozzle 52, and is entrained into the air stream in the endotracheal tube, and distributed throughout the lungs of the patient. Because of its aerosol form, the medication is distributed over a large surface area, and is rapidly taken up.

A second embodiment of an improved endotracheal tube constructed according to the principles of this invention is indicated generally as 20' in FIG. 4. The endotracheal tube 20' is similar in construction to endotracheal tube 20, and corresponding parts are identified with corresponding reference numerals. The chief difference between tubes 20' and 20, is that in tube 20' the injector 46 and nozzle 52 are not located adjacent the distal end.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:
1. An endotracheal tube comprising:
   a hollow tubular body having a proximal end, a distal end for insertion into the trachea of a patient, the hollow tubular body having a longitudinal axis extending between the proximal and distal ends,
   an aerosol medication lumen, having proximal and distal ends, and extending along at least a portion of the tubular body;
   a nozzle at the distal end of the lumen, inside the tubular body;
   means for connecting the proximal end of the lumen to a canister having a supply of aerosol propellant and medication therein, to dispense the medication in aerosol form from the nozzle in the endotracheal tube;

an injector having opposite end portions extending generally transversely and entirely across the tubular body and generally perpendicular to the longitudinal axis of the tubular body to form a diametrical chord for the tubular body with at least one of the opposite end portions being fixed to the tubular body, and wherein the nozzle is located in the injector.

2. The endotracheal tube according to claim 1 wherein the nozzle is located adjacent the distal end of the tubular body.

3. The endotracheal tube according to claim 1 wherein the nozzle is located in the injector at a position generally at the center of the tubular body.

4. The endotracheal tube according to claim 3 wherein the nozzle is oriented to face generally outwardly toward the distal end of the tubular body.

5. An endotracheal tube according to claim 1 wherein the aerosol medication lumen extends along at least a portion of the tubular body generally in the direction of the longitudinal axis of the tubular body.

6. In combination, a metered dose inhaler (MDI) having aerosol propellant and medication therein and having a valve including a valve volume; and an endotracheal tube comprising a hollow tubular body having a proximal end, a distal end for insertion into the trachea of a patient, the hollow tubular body defining a longitudinal axis extending between the proximal and distal ends, an aerosol medication lumen having a lumen diameter and length and having proximal and distal ends, an injector having a nozzle at the distal end of the lumen, inside the tubular body and adjacent the distal end of the tubular body; the nozzle having an orifice diameter, the injector extending transversely and entirely across the tubular body in a direction that is generally perpendicular to the longitudinal axis, and means for connecting the proximal end of the lumen to the metered dose inhaler (MDI); and wherein the valve volume, orifice diameter, lumen diameter and lumen length are selected to dispense a respirable mass of the medication in aerosol form from the nozzle in the endotracheal tube.

7. A combination according to claim 6 wherein the injector has opposite end portions, and the injector forms a diametrical chord for the tubular body with at least one of the opposite end portions being fixed to the tubular body.

8. A combination according to claim 7 wherein the nozzle is located in the injector at a position generally at the center of the tubular body and is positioned to face generally outwardly toward the distal end of the tubular body to direct medicament in a direction generally parallel to the longitudinal axis of the tubular body.

9. A combination according to claim 6 wherein the nozzle is located adjacent the distal end of the tubular body.

10. A combination according to claim 6 wherein:
the orifice diameter is approximately 100 mils, the lumen diameter is approximately 2.92 millimeters, the lumen length is selected from the group of approximately 152.4 or 304.8 millimeters, and the MDI valve volume is selected from the group consisting of approximately 25 ul, 50 ul, 63 ul or 100 ul.

11. A combination according to claim 6 wherein:
the orifice diameter is approximately 33 mils, the lumen diameter is approximately 1.19 millimeters, the lumen length is approximately 152.4 millimeters and the MDI valve volume is about 100 ul.

12. A combination according to claim 6 wherein:
the orifice diameter is approximately 5 mils, the lumen diameter is approximately 1.14 millimeters, the lumen length is selected from the group of approximately 152.4 or 304.8 millimeters, and the MDI valve volume is approximately 100 ul.

* * * * *